United States Patent
Im et al.

(10) Patent No.: US 9,222,884 B2
(45) Date of Patent: Dec. 29, 2015

(54) HYDROGEN PEROXIDE SENSITIVE METAL NANOPARTICLES, METHOD FOR PRODUCING THE SAME AND HYDROGEN PEROXIDE DETECTION SYSTEM COMPRISING THE SAME

(71) Applicants: Samsung Electronics Co., Ltd., Suwon-si (KR); POSTECH ACADEMY-INDUSTRY FOUNDATION, Pohang-si (KR)

(72) Inventors: Kyu-hyun Im, Yongin-si (KR); No-kyoung Park, Hwaseong-si (KR); Jae-hyun Hur, Yongin-si (KR); Sung-jee Kim, Pohang-si (KR); Ju-taek Nam, Pohang-si (KR); Seong-ho Park, Pohang-si (KR); Sang-hwa Jeong, Pohang-si (KR)

(73) Assignees: SAMSUNG ELECTRONICS CO., LTD., Suwon-si (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 14/015,147

(22) Filed: Aug. 30, 2013

(65) Prior Publication Data

US 2014/0065718 A1   Mar. 6, 2014

(30) Foreign Application Priority Data

Sep. 5, 2012   (KR) .................. 10-2012-0098418

(51) Int. Cl.
  *G01N 21/59*   (2006.01)
  *G01N 21/25*   (2006.01)
  (Continued)

(52) U.S. Cl.
  CPC    *G01N 21/59* (2013.01); *C01G 7/00* (2013.01); *B82Y 30/00* (2013.01); *B82Y 40/00* (2013.01); *G01N 21/25* (2013.01); *G01N 2021/5903* (2013.01); *Y10S 977/70* (2013.01); *Y10S 977/773* (2013.01); *Y10S 977/81* (2013.01); *Y10S 977/896* (2013.01); *Y10S 977/915* (2013.01);
  (Continued)

(58) Field of Classification Search
  CPC ......... G01N 21/59; G01N 21/00; C01G 7/00; B82Y 40/00; Y10T 436/00; Y10T 436/20; Y10T 436/206664; Y10S 977/773; Y10S 977/70; Y10S 977/00; Y10S 977/81; Y10S 977/896; Y10S 977/873
  USPC ................ 436/135, 127; 422/82.09, 68.1, 50; 977/773, 810, 896, 920
  See application file for complete search history.

(56) References Cited

FOREIGN PATENT DOCUMENTS

JP    2002-508337 A    3/2002
KR    10-2008-0020672 A    3/2008
(Continued)

OTHER PUBLICATIONS

Manivannan, Shanmugam et al., Core-shell Au/Ag nanoparticles embedded in silicate sol-gel netowrk for sensor application towards hydrogen peroxide, J. Chem. Sci., vol. 121, No. 5, Sep. 2009, pp. 735-743.*

(Continued)

*Primary Examiner* — Christine T Mui
(74) *Attorney, Agent, or Firm* — Sughrue Mion, PLLC (57) ABSTRACT

Provided is a hydrogen peroxide sensitive metal nanoparticle including: a metal nanoparticle including a biocompatible metal and a hydrogen peroxide reactive ion which is bonded to a surface of the metal nanoparticle and is oxidized by hydrogen peroxide.

24 Claims, 5 Drawing Sheets (51) Int. Cl.
*G01N 21/00* (2006.01)
*B82Y 40/00* (2011.01)
*C01G 7/00* (2006.01)
*B82Y 30/00* (2011.01)

(52) U.S. Cl.
CPC .......... *Y10S 977/92* (2013.01); *Y10T 428/2982* (2015.01); *Y10T 436/20* (2015.01); *Y10T 436/206664* (2015.01)

(56) References Cited

FOREIGN PATENT DOCUMENTS

| KR | 10-2008-0095182 A | 10/2008 |
|---|---|---|
| KR | 10-2010-0123795 A | 11/2010 |
| KR | 10-2011-0038215 A | 4/2011 |
| KR | 10-2013-0129704 A | 11/2013 |
| WO | 99/30741 A2 | 6/1999 |

OTHER PUBLICATIONS

Guo, Ji-Zhao et al., Ag nanoparticle-catalyzed chemiluminescent reaction between luminol and hydrogen peroxide, Journal of Photochemistry and Photobiology A: Chemistry, 193, 2008, pp. 89-96.*

Liu Sen et al., Microwave-assisted rapid synthesis of Ag nanoparticles/graphene nanosheet composites and their application for hydrogen peroxide detection, J Nanopart Res, 2011, 13:4539-4548.*

Zhang, Taiji et al., Biotemplated Synthesis of Gold Nanoparticle-Bacteria Cellulose Nanofiber Nanocomposites and Their Application in Biosensing, Adv. Fund. Mater., 2010, 20, 1152-1160.*

Cheng, Wenlong et al., Iodine-Induced Gold-Nanoparticle Fusion/Fragmentation/Aggregation and Iodine-Linked Nanostructured Assemblies on a Glass Substrate, Angew. Chem. Int. Ed., 2003, 42, 4, 449-452.*

* cited by examiner

HYDROGEN PEROXIDE SENSITIVE METAL NANOPARTICLES, METHOD FOR PRODUCING THE SAME AND HYDROGEN PEROXIDE DETECTION SYSTEM COMPRISING THE SAME

CROSS-REFERENCE TO RELATED APPLICATIONS

This application claims benefit to Korean Patent Application No. 10-2012-0098418, filed on Sep. 5, 2012 in the Korean Intellectual Property Office, the disclosure of which is incorporated by reference herein in its entirety.

BACKGROUND

1. Field

Disclosed is a metal nanoparticle that may be used for photothermal therapy, and a method for producing the same.

2. Description of the Related Art

Numerous free electrons exist inside metal conductors. Since such free electrons are not bound to metal atoms, and thus they may easily respond to a specific stimulus from an external environment. In particular, in the case of nano-sized metals, surface plasmon resonance characteristics appear as a result of the behavior of free electrons, giving unique optical characteristics to metal nanoparticles. Surface plasmon is a phenomenon in which electrons in a metal oscillate as a group when light is incident between the surfaces of conducive metal nanoparticles and dielectric materials, such as air or water, and the oscillation frequency of the electrons vibrating with respect to the nucleus resonate with a certain specific frequency of incident light. The interaction between light and metal nanoparticles is very strong and metal nanoparticles have a much higher absorption coefficient than regular organic dyes at a resonance frequency. Since the resonance frequency varies based on the size, form, or surface characteristics of particles and dispersed solvents, efforts to make metal nanoparticles having various sizes, forms, and surface characteristics are in progress in order to apply such metal nanoparticles to, for example, optical sensors or light condensers.

Recently, photothermal therapy utilizing the light condensing effect of gold nanoparticles has arisen as a potential biotechnical application. Photothermal therapy is a therapeutic method in which light energy is converted into heat energy that attacks the cells that are to be treated. The light condensed on the surface of gold nanoparticles may be emitted via various routes, including the heat-accompanied processes of electron-lattice vibration and electron-electron scattering. Then, the heat energy that is locally emitted from the gold nanoparticles may be sufficient to kill target cells because of the excellent light condensing effect and the large surface area to volume ratio of gold nanoparticles. In addition, when the local heat emission is controlled by selectively limiting or increasing the amount of light that is condensed on the gold nanoparticles, this permits for the selective treatment or killing of cancer cells or cells of inflammatory sites while leaving normal cells undamaged.

A nano structure useful in cancer selective photothermal therapy, using a pH or temperature sensitive surface ligand to alter the surface structure or surface electron charge of gold nanoparticles, is also being developed. However, there remain problems to be solved, such as the toxicity that results from surface ligands that are not naturally present in the circulatory system.

SUMMARY

Provided herein are metal nanoparticles that may be used in the photothermal therapy of cells.

Provided herein are methods of manufacturing metal nanoparticles that may be used for the photothermal therapy of cells.

Provided herein are detection systems that may detect hydrogen peroxide.

Additional aspects will be set forth in part in the description which follows and, in part, will be apparent from the description, or may be learned by practice of the presented embodiments.

According to an aspect, a metal nanoparticle includes a biocompatible metal and a hydrogen peroxide reactive ion that is bonded to a surface of the metal nanoparticle and may be oxidized by hydrogen peroxide.

The biocompatible metal may include gold (Au), platinum (Pt), silver (Ag), titanium (Ti), or alloys thereof.

The metal nanoparticles may have a diameter of approximately 5 to approximately 10 nm.

The hydrogen peroxide reactive ion may include an iodide ion, $I^-$.

The metal nanoparticles may react with hydrogen peroxide to form an agglomerate. The agglomerate may have a size within the range of approximately 50 to approximately 600 nm.

The agglomerates of the metal nanoparticles may have a light absorbance which is higher than the light absorbance of the metal nanoparticles prior to the forming of the agglomerate in both the visible light wavelength band of not less than about 600 nm and the infrared wavelength band.

The agglomerates may produce heat when irradiated with light in the visible light wavelength band of not less than about 600 nm and the near-infrared wavelength band.

According to another aspect, a method of manufacturing a hydrogen peroxide sensitive metal nanoparticle includes: manufacturing a metal nanoparticle with a stabilizing ligand bonded to the surface thereof; and replacing the stabilizing ligand with a hydrogen peroxide reactive ion, which may be oxidized by hydrogen peroxide.

The manufacturing of the metal nanoparticle may include: dissolving a metal precursor in a solvent to form a metal precursor solution; and adding a reductant to the metal precursor solution to reduce the metal precursor.

According to another aspect, a hydrogen peroxide detecting system includes: a medium containing the above hydrogen peroxide sensitive metal nanoparticle; a laser light irradiating the medium; and a temperature measuring device measuring the temperature of the medium. The laser light may have a wavelength within the range of approximately 600 to approximately 1100 nm.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

The term "nanoparticle" as used herein refers to particles with at least a 1-dimensional size of about 5 nm to about 100 nm.

The term "hydrogen peroxide reactive ion" as used herein refers to ions that change their electric charge characteristic via oxidation with hydrogen peroxide.

The term "hydrogen peroxide sensitive metal nanoparticle" as used herein refers to metal nanoparticles that react with hydrogen peroxide in a hydrogen peroxide environment to form an agglomerate of such metal nanoparticles via a change in the surface energy of the metal nanoparticles, thus changing the surface plasmon characteristics and optical characteristics of the metal nanoparticles, which can enhance the photothermal therapy effect.

The term "biocompatible" or "biocompatibility" as used herein refers to a material's ability to be used in close contact with a living body without a harmfully influencing the living body.

The term "metal nanoparticle stabilizing ligand" as used herein refers to ligands forming coordinate bonds with nanoparticles. Metal nanoparticle stabilizing ligands enable metal nanoparticles to exist in uniform distribution in a solution without forming agglomerates via the reduction of the surface energy of metal nanoparticles.

The term "citrate ligand gold nanoparticle" as used herein refers to a gold nanoparticle having a citrate ligand bonded to its surface.

Figure 1:
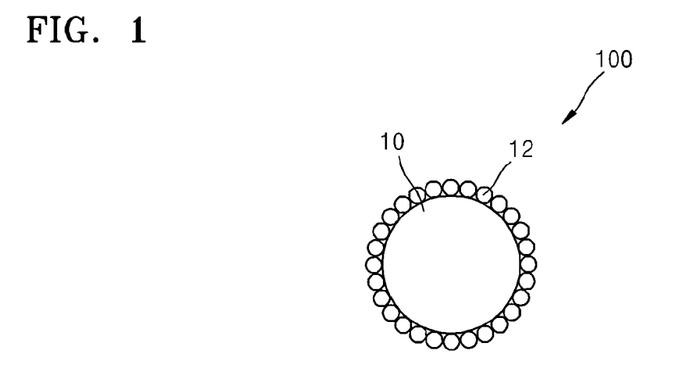
FIG. 1 is a schematic view conceptually showing hydrogen peroxide sensitive metal nanoparticles 100 according to an embodiment.

FIG. 1 is a schematic view conceptually showing a hydrogen peroxide sensitive metal nanoparticle 100 according to an embodiment.

Referring to FIG. 1, the hydrogen peroxide sensitive metal nanoparticle 100 includes a metal nanoparticle 10 and hydrogen peroxide reactive ions 12 adsorbed to the metal nanoparticle 10.

The metal nanoparticle 10 may be a metal particle or a particle having a metal coated thereon, such as silica. The metal may be biocompatible. The biocompatible metal may be, for example, gold (Au), platinum (Pt), silver (Ag), titanium (Ti), or alloys thereof. The metal nanoparticle 10 may have a diameter within the range of from approximately 5 to approximately 100 nm. When the metal nanoparticle 10 has a diameter within this range, it may be suitable for movement within a body or cell uptake.

Hydrogen peroxide reactive ions 12 are ions that may be oxidized via a reaction with hydrogen peroxide, and are adsorbed on the surface of the metal nanoparticle 10. The hydrogen peroxide reactive ions 12 may cover the entire surface of the metal nanoparticle 10. The hydrogen peroxide reactive ions 12 may be, for example, iodide ions, I$^-$, that may be oxidized via a reaction with hydrogen peroxide. The hydrogen peroxide sensitive metal nanoparticle 100 having the hydrogen peroxide reactive ions 12 adsorbed thereon has a negative electric charge and may maintain its surface stability via electrostatic repulsive force.

The hydrogen peroxide reactive ions 12 may be removed or disassociate from the surface of the metal nanoparticle 10 as a result of the loss of their electrical charge after oxidization by hydrogen peroxide. Once the hydrogen peroxide reactive ions 12 are removed, the surface stability of the metal nanoparticle 10 is decreased and hence the metal nanoparticles 10 may coagulate.

The optical characteristics of the hydrogen peroxide sensitive metal nanoparticles 100 may change as a result of a change in surface plasmon characteristics once the hydrogen peroxide sensitive metal nanoparticles coagulate. In particular, the light absorbance wavelength may be shifted to a longer wavelength (i.e., a red shift), and the light absorbance may be increased in the wavelength range of approximately 600 to approximately 1100 nm. The light absorbance may be increased by approximately 50-100%.

Such a shift in the light absorbance wavelength of the hydrogen peroxide sensitive metal nanoparticles 100 enables the hydrogen peroxide sensitive metal nanoparticles 100 to be used in photothermal therapy. The use of the hydrogen peroxide sensitive metal nanoparticles 100 in photothermal therapy will now be explained in detail.

In general, various types of oxidases in cells are involved in inflammation response or the survival of cancer cells, and a large quantity of hydrogen peroxide, $H_2O_2$, is produced by these oxidases. Oxidases that are involved in inflammation response and the survival of cancer cells include cyclooxygenase, lipoxygenase and the like. These oxidases produce superoxide, $O^{2-}$, which reacts with surrounding water to produce hydrogen peroxide.

Taking the process of thyroid hormone production in thyroid vesicles as an example, vesicular cells constituting the thyroid vesicle collect the iodide ions in blood into cells by using an iodide pump, while producing a high concentration of hydrogen peroxide at the same time. Then, thyroid peroxidase synthesizes the thyroid hormone by using hydrogen peroxide to bind iodine with thyroxine in thioglobulin molecules. However, when thyroid cancer or hyperthyroidism occurs, the thyroid gland partially enlarges, and thus an abnormally large amount of hydrogen peroxide may be produced in the thyroid vesicles in such circumstances.

At such a time, when hydrogen peroxide sensitive metal nanoparticles 100 according to the present embodiment exist near inflamed cells or cancer tissue cells, the hydrogen peroxide reactive ions 12 are oxidized by the hydrogen peroxide produced by the cells and are removed from the surface of the hydrogen peroxide sensitive metal nanoparticles 100. The hydrogen peroxide sensitive metal nanoparticles 100 from which the hydrogen peroxide reactive ions 12 have been removed will form agglomerates by coagulating with nearby nanoparticles to reduce their surface energy. The agglomerates may have a size within the range of approximately 50 to approximately 600 nm. The hydrogen peroxide sensitive metal nanoparticles 100 exhibit different light absorbance characteristics after coagulation than they do before coagulation.

When hydrogen peroxide sensitive metal nanoparticles 100 are coagulated in the presence of hydrogen peroxide, the maximum light absorbance wavelength thereof is shifted toward a longer wavelength as a result of a change in surface plasmon characteristics, as compared with their status prior to the formation of the agglomerates. As a result of the shifting, the light absorbance of the hydrogen peroxide sensitive metal nanoparticles 100 is increased in the visible light wavelength band of not less than about 600 nm and in the infrared wavelength band. Accordingly, when external laser light having a high tissue transmittance in a long wavelength band of visible light or in the infrared wavelength band are irradiated onto the hydrogen peroxide sensitive metal nanoparticles 100, the hydrogen peroxide sensitive metal nanoparticles 100 may absorb the laser light and locally generate heat.

In this regard, cancer cells lack blood supply as compared to normal cells, and hence have lower heat resistance, and are destroyed at 41-47° C. as a result of loosened cell membranes and denatured proteins. In the present embodiment, the hydrogen peroxide sensitive metal nanoparticles 100 may be agglomerated to locally generate heat only in regions with an abnormally high amount of hydrogen peroxide, i.e., only in regions with inflamed or tumor cells, such that other nearby organs are not influenced. Furthermore, other nearby organs, containing normal cells, are not influenced in the temperature range of 41-47° C. Therefore, it is expected that effective photothermal therapy may be possible by controlling the heat generated by the hydrogen peroxide sensitive metal nanoparticles 100. The heat generation achieved by the hydrogen peroxide sensitive metal nanoparticles 100 may be controlled by adjusting the size of the hydrogen peroxide sensitive metal particles 100, the types of surface ligand 11, the hydrogen peroxide reactive ions 12, or the solvent.

Meanwhile, when the hydrogen peroxide sensitive metal nanoparticles 100 are introduced into cells to form agglomerates, since the exocytosis of cells is inhibited as a result of the increase in size of the hydrogen peroxide sensitive metal nanoparticles 100, which may serve to inhibit the discharge of the hydrogen peroxide sensitive metal nanoparticles 100, the efficiency of photothermal therapy may be enhanced.

As previously explained, agglomerates of the hydrogen peroxide sensitive metal nanoparticles 100 caused by an inflammation response or accumulated in cancer tissue cells act as small heat sources and generate heat only in local regions, which may minimize side effects on normal tissues. In addition, since the hydrogen peroxide sensitive metal nanoparticles 100 may use iodide ions, $I^-$, which already exist in a living body's circulatory system, as the hydrogen peroxide reactive ions 12, potential cellular toxicity problems may be avoided. Moreover, the hydrogen peroxide reactive ion 12 is advantageous because it is not a macromolecule, but is instead a very simple system.

Figure 2:
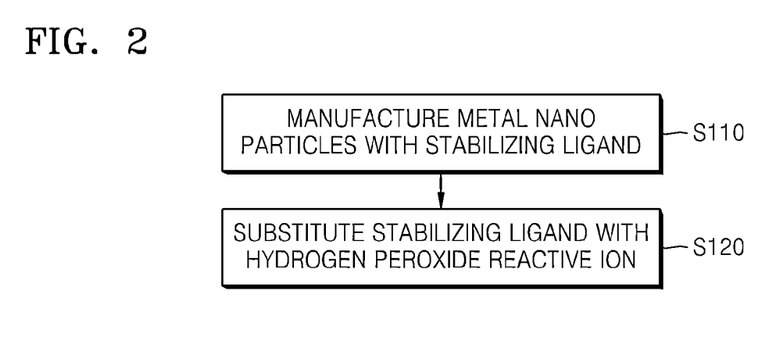
FIG. 2 is a flow chart showing a method of manufacturing a hydrogen peroxide sensitive metal nanoparticle.

FIG. 2 is a flow chart showing a method of manufacturing a hydrogen peroxide sensitive metal nanoparticle according to an embodiment.

Referring to FIG. 2, first a metal nanoparticle with a stabilizing ligand is manufactured (S110). The metal nanoparticle with the stabilizing ligand may be manufactured via, for example, a metal ion reduction method. A metal ion reduction method is a method of producing metal nanoparticles having stabilizing ligands in a hydrosol form by using a reducing agent or surfactants after dissociating the metal precursor of a metal compound in solution (solvent).

As metal compounds that are a precursor of a metal, chloroauric acid $HAuCl_4$, silver nitrate $AgNO_3$, platinum(IV) chloride $PtCl_4$, titanium butoxide $Ti(Obu)_4$, and the like may be used. As a reducing agent, trisodium citrate $Na_3C_6H_5O_7$, sodium borohydride ($NaBH_4$), and the like. may be used. As a surfactant, commercial surfactants that are used for manufacturing metal nanoparticles may be used, or may be omitted in some cases. Examples of solvents that dissociate metal compounds are water and alcohol, but the solvents are not limited thereto.

The metal nanoparticles manufactured by the metal ion reduction method may form a stable colloid liquid via formation by a reductant of stabilizing ligands on a surface of the metal nanoparticles. The stabilizing ligands may stabilize the surface of the metal nanoparticles and may include an alkyl thiolate ligand or aryl thiolate ligand, but are not limited thereto. The ligands formed on the surface of the nanoparticle may be selectively exchanged with other stabilizing ligands via ligand exchange. The reductant may comprise, for example, trisodium citrate, lithium aluminum hydride (LiAlH$_4$), nascent atomic hydrogen, sodium amalgam, sodium borohydride (NaBH$_4$), tin (II) chloride, sodium sulfide (Na$_2$S), hydrazine (N$_2$H$_4$), zinc-mercury amalgam (Zn(Hg)), diisobutylaluminum hydride (DIBAH), Lindlar's catalyst, an oxalic acid (C$_2$H$_2$O$_4$), a formic acid (HCOOH) or an ascorbic acid (C$_6$H$_8$O$_6$).

Next, stabilizing ligands of metal nanoparticles are replaced by ions that react with hydrogen peroxide (S120). For this, a solution of ions that react with hydrogen peroxide is added at, e.g., room temperature, to a solution of metal nanoparticles with ligands. Then, the ions that react with hydrogen peroxide may replace the ligands on the surface of metal nanoparticles and thus provide hydrogen peroxide sensitive metal nanoparticles having ions adsorbed on the surface thereof.

Meanwhile, optical characteristics of the hydrogen peroxide sensitive metal nanoparticles that are effective for photothermal therapy may be controlled by adjusting the sizes of the hydrogen peroxide sensitive metal nanoparticles, the hydrogen peroxide reactive ions that are used, the solvents, etc.

Figure 3:
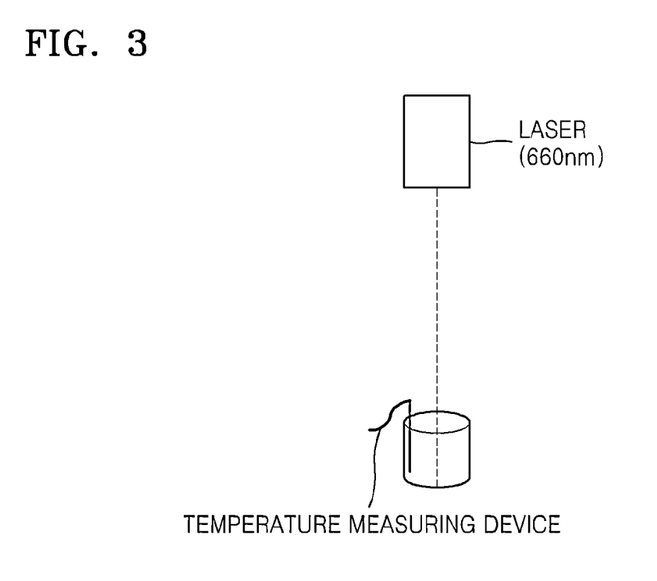
FIG. 3 is a diagram showing a hydrogen peroxide detecting system according to an embodiment.

FIG. 3 is a diagram showing a hydrogen peroxide detecting system according to an embodiment.

Referring to FIG. 3, a hydrogen peroxide detecting system according to an embodiment includes a medium including the hydrogen peroxide sensitive metal nanoparticles described herein, a laser light irradiated onto the medium and having a wavelength of over 600 nm, for example, a wavelength ranging from 660-1100 nm, and a temperature measuring device measuring the temperature of the medium.

The medium may include water, a cell culture medium, and the like. The hydrogen peroxide sensitive metal nanoparticles may be distributed within the medium. In the case where the medium includes hydrogen peroxide, hydrogen peroxide sensitive metal nanoparticles react with the hydrogen peroxide and form agglomerates; consequently the temperature of the medium increases when the laser light is irradiated to the medium. Therefore the temperature of the medium may be measured and used to determine whether hydrogen peroxide is present in the medium. As the temperature measuring device, a thermocouple, thermistor, or resistance temperature detector may be used, for example.

EXAMPLES (a) Manufacture of Citrate Ligand Gold Nanoparticles

Figure 4:
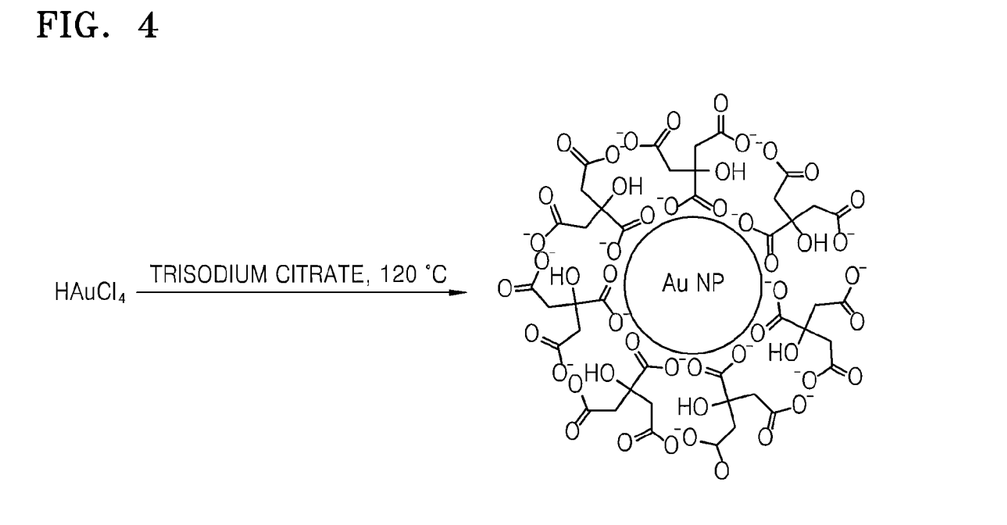
FIG. 4 is a diagram conceptually showing a process of manufacturing a citrate ligand gold nanoparticle.

A process of manufacturing citrate ligand gold nanoparticles is conceptually shown in FIG. 4. After heating a solution of 0.0849 g of a precursor of gold, chloroauric acid $HAuCl_4$, dissolved in 500 ml of distilled water for 30 minutes in a 120° C. oil bath while stirring, 0.2205 g of trisodium citrate was added, followed by an additional two hours of heating in the 120° C. oil bath. The trisodium citrate works as both a reductant and a surface ligand of gold nanoparticles, and the production of citrate ligand gold nanoparticles was identified by a change in color of the solution from yellow to red. Afterwards, the citrate ligand gold nanoparticles were cooled at room temperature while stirring.

(b) Manufacture of Hydrogen Peroxide Sensitive Gold Nanoparticles

Figure 5:
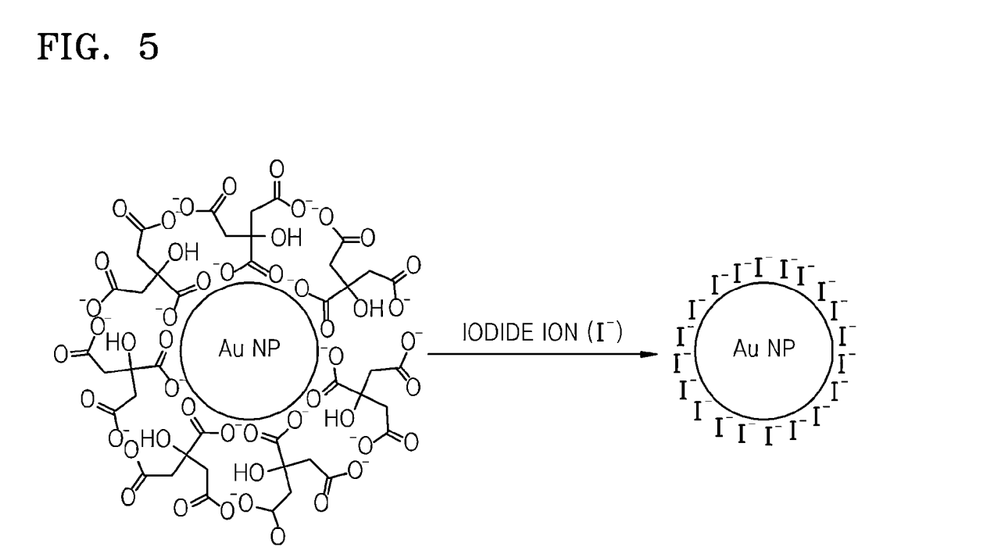
FIG. 5 is a diagram conceptually showing a process of manufacturing gold nanoparticles adsorbed with iodide ions.

The process of manufacturing gold nanoparticles adsorbed with iodide ions is conceptually shown in FIG. 5. 8 μg of 0.2M iodide ion solution was added to a solution of citrate ligand gold nanoparticles at room temperature. Within a few minutes at room temperature, the citrate ligands present on the surfaces of the gold nanoparticles were replaced by the iodide ions to form ligand gold nanoparticles ed with iodide ions. Replacement of the citrate ligands with the iodide ions was indirectly identified based on an approximate 5 nm shift toward a longer wavelength of the light absorbance spectrum wavelength of the gold nanoparticles. The gold nanoparticles adsorbed with iodide ions are hydrogen peroxide sensitive metal nanoparticles that may sensitively react to hydrogen peroxide.

Light Absorbance Spectrum

Figure 6:
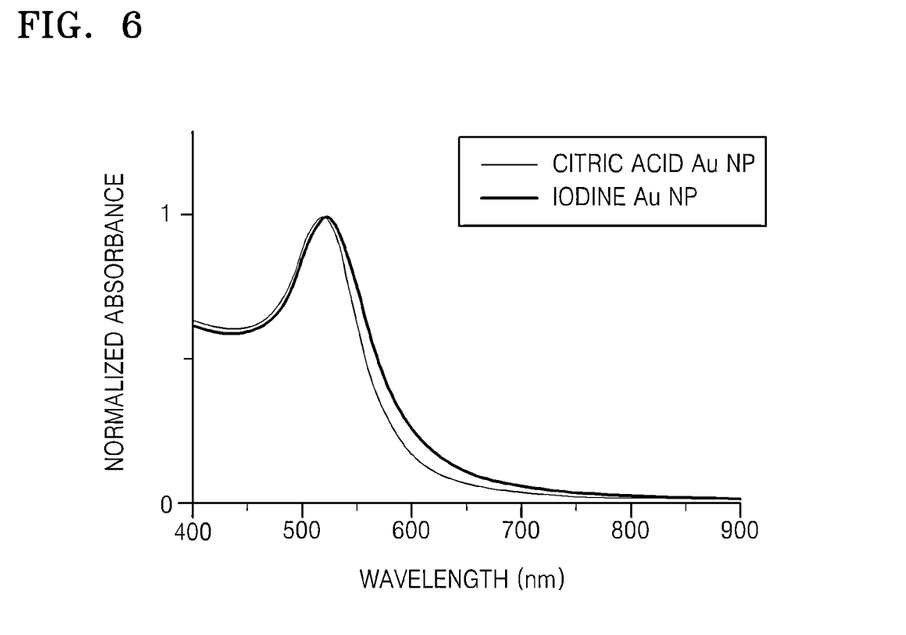
FIG. 6 shows light absorbance spectra according to wavelengths of citrate ligand gold nanoparticles and gold nanoparticles adsorbed with iodide ions.

FIG. 6 is a light absorbance spectrum showing normalized absorbance as a function of wavelength for citrate ligand gold nanoparticles (Citric Acid Au NP) and gold nanoparticles adsorbed with iodide ions (Iodine Au NP). The citrate ligand gold nanoparticles were manufactured via the process in example (a) above, and gold nanoparticles adsorbed with iodide ions were manufactured via the process in example (b) above. The light absorbance spectrum was acquired by measuring light absorbance while irradiating sample solutions of Citrate Au NP and Iodine Au NP with light having wavelengths from 400 nm to 900 nm. Referring to FIG. 6, the absorbance peak of gold nanoparticles adsorbed with iodide ions is shifted towards a longer wavelength as compared to the absorbance peak of citrate ligand gold nanoparticles.

Figure 7:
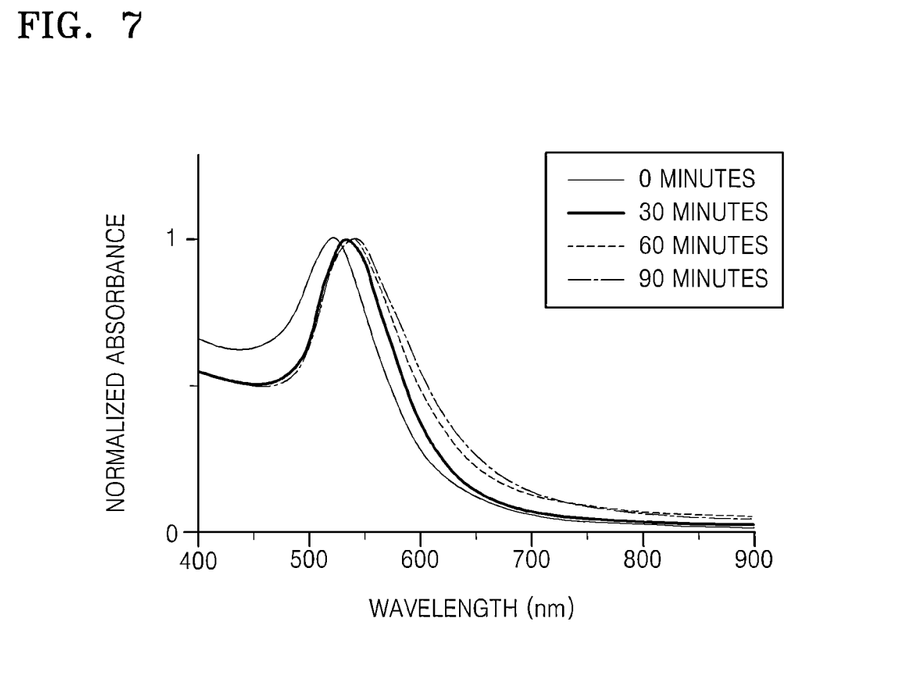
FIG. 7 shows light absorbance spectra of gold nanoparticles adsorbed with iodide ions as measured based on the length of time the gold nanoparticles were exposed to a hydrogen peroxide environment.

FIG. 7 is a light absorbance spectrum showing normalized absorbance as a function of wavelength for gold nanoparticles adsorbed with iodide ions, measured based on the reported length of time the gold nanoparticles were exposed to a hydrogen peroxide environment. The hydrogen peroxide environment was prepared by adding 3 μl of 1M hydrogen peroxide solution to 1 ml of a 30 nM solution of gold nanoparticles adsorbed with iodide ions, and light absorbance was measured at 0 minutes, 30 minutes, 60 minutes and 90 minutes after adding the 3 μl of 1M hydrogen peroxide solution.

Referring to FIG. 6, gold nanoparticles adsorbed with iodide ions showed a peak in the absorbance spectrum at a wavelength of approximately 520 nm in an environment of a colloid free of hydrogen peroxide. However, referring to FIG. 7, it may be seen that the peak in the absorbance spectrum of gold nanoparticles adsorbed with iodide ions shifted toward the longer wavelengths as time elapsed after hydrogen peroxide was added to the solution of gold nanoparticles adsorbed with iodide ions.

The shifting of the peak in the absorbance spectrum of the gold nanoparticles towards the longer wavelength is considered to be a consequence of gold nanoparticles adsorbed with iodide ions forming agglomerates as they become unstable due to the removal of iodide ions from the surface of gold nanoparticles as a result of oxidation with hydrogen peroxide. In general, when gold nanoparticles form agglomerates, the peak of the absorbance spectrum of the gold nanoparticles shifts towards longer wavelengths due to characteristic of surface plasmon. Therefore the fact that gold nanoparticles adsorbed with iodide ions form agglomerates by reacting with hydrogen peroxide may be identified by the shifting of the absorbance spectrum shown in, for example, FIG. 7.

Transmission Electron Microscope (TEM) Photographs

Figure 8:
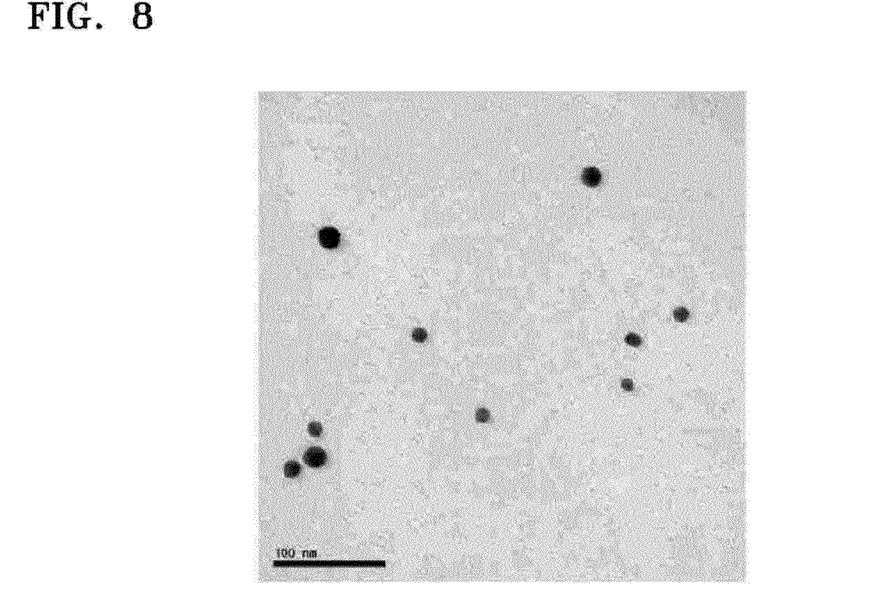
FIG. 8 is a transmission electron microscope (TEM) photograph taken immediately after exposure of gold nanoparticles adsorbed with iodide ions to the hydrogen peroxide environment.
Figure 9:
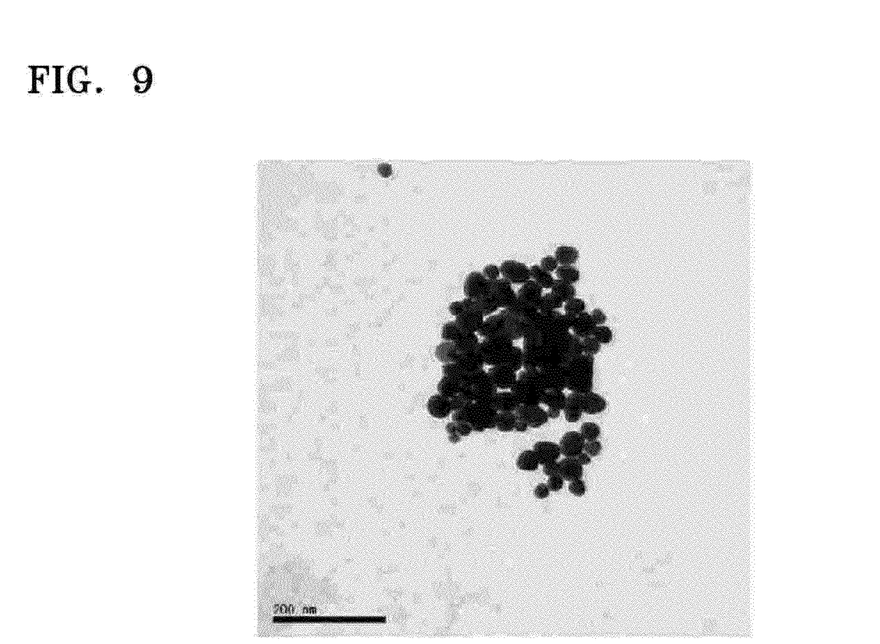
FIG. 9 is a TEM photograph taken after elapse of 30 minutes from exposure of gold nanoparticles adsorbed with iodide ions to the hydrogen peroxide environment.

FIG. 8 is a TEM photograph taken after immediate exposure (0 minutes) of gold nanoparticles adsorbed with iodide ions to a hydrogen peroxide environment. FIG. 9 is a TEM photograph taken after gold nanoparticles adsorbed with iodide ions had been exposed to the hydrogen peroxide environment for 30 minutes.

Referring to the TEM photograph of FIG. 8, immediately (i.e., at 0 minutes) after exposure to the hydrogen peroxide environment, it may be seen that gold nanoparticles adsorbed with iodide ions are evenly distributed within the solution, with an average particle size of about 15 nm.

However, referring to the TEM photograph of FIG. 9, it may be seen that gold nanoparticles adsorbed with iodine ions form larger agglomerates, up to a few hundred nm in size, after 30 minutes of exposure to the hydrogen peroxide environment.

Photothermal Change Measurement

Figure 10:
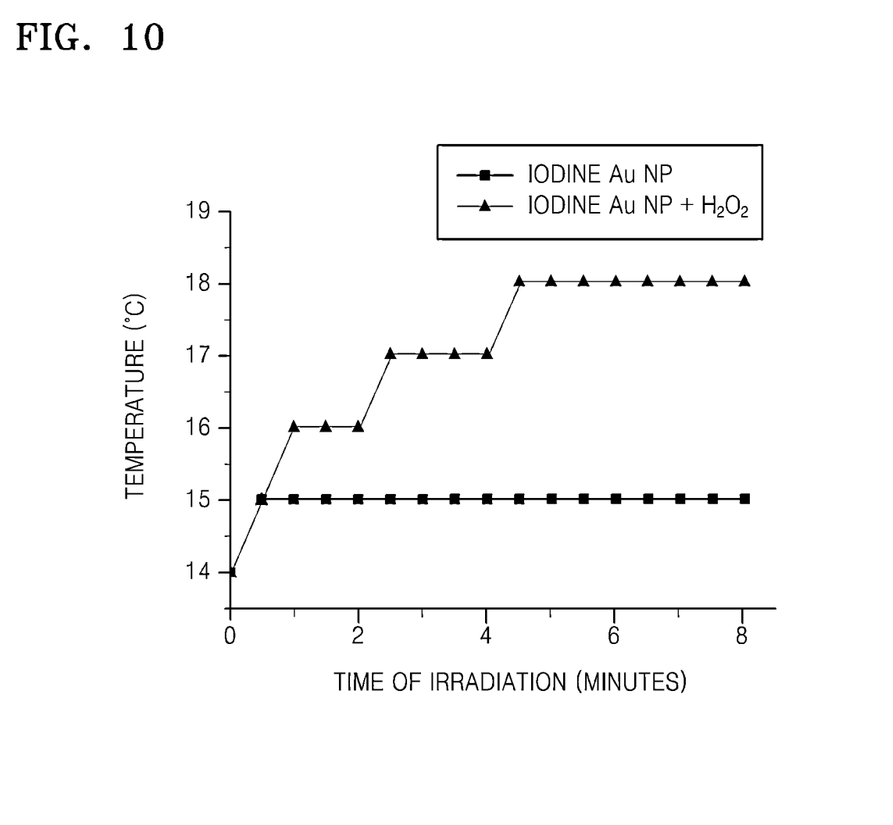
FIG. 10 is a graph showing a change in temperature of gold nanoparticles adsorbed with iodide ions depending on light irradiation time in the presence of hydrogen peroxide and in the absence of hydrogen peroxide.

FIG. 10 is a graph showing the temperature change of gold nanoparticles adsorbed with iodide ions as a function of irradiation time for an embodiment in the presence of hydrogen peroxide and an embodiment in the absence of hydrogen peroxide.

In FIG. 10, a sample iodine coated Au $NP+H_2O_2$ was used as experimental group wherein 90 minutes had elapsed after having added 3 μl of 1M hydrogen peroxide to 1 ml of a 30 nM solution of gold nanoparticles adsorbed with iodine. A sample iodine coated Au NP of 1 ml of a 30 nM solution that included only gold nanoparticles adsorbed with iodine was used as control group. Laser light having a wavelength of 660 nm and a power of 8.20 $W/cm^2$ was irradiated onto samples of the experimental group and the control group for 10 minutes, and the temperature changes of the two samples were observed and recorded over the first 8 minutes. The temperature of the samples was measured with a thermocouple. Referring to the graph of FIG. 10, an increase in temperature is observed in the experimental group over time, but the temperature remains constant in the control group. Based on these experimental results, it is shown that using a laser to irradiate hydrogen peroxide sensitive gold nanoparticles in a hydrogen peroxide environment will increase the temperature thereof and hence hydrogen peroxide sensitive metal nanoparticles may be used effectively for photothermal therapy for inducing cell death.

As described above, according to the one or more of the above embodiments, hydrogen peroxide sensitive metal nanoparticles may be used effectively for photothermal therapy by increasing heat emission efficiency, which is a result of enhancing the light absorbance at a longer wavelength band of visible and infrared light by shifting the light absorbance wavelength to the longer wavelength via the formation of agglomerates resulting from a reaction with hydrogen peroxide. The hydrogen peroxide sensitive metal nanoparticles herein may solve toxicity related problems by employing ions that naturally exist in the body's circulatory system, and may be formed as a simple structure of simple ions attached to the surface of metal nanoparticles.

It should be understood that the exemplary embodiments described herein should be considered to be descriptive only and not limiting. Descriptions of features or aspects within each embodiment should typically be considered as being available for similar features or aspects in other embodiments.

What is claimed is:

1. A hydrogen peroxide sensitive metal nanoparticle comprising:
    a metal nanoparticle including a biocompatible metal; and
    a hydrogen peroxide reactive ion which is bonded to a surface of the metal nanoparticle and is capable of being oxidized by hydrogen peroxide, and
    the hydrogen peroxide sensitive metal nanoparticle forms an agglomerate with other hydrogen peroxide sensitive metal nanoparticles after a reaction with hydrogen peroxide, and
    wherein the hydrogen peroxide reactive ion is adsorbed onto the metal nanoparticle, and the hydrogen peroxide reactive ion comprises an iodide ion, $I^-$.

2. The hydrogen peroxide sensitive metal nanoparticle of claim 1, wherein the metal nanoparticle comprises a metal or a metal coated on silica.

3. The hydrogen peroxide sensitive metal nanoparticle of claim 1, wherein the biocompatible metal comprises gold, platinum, silver, titanium or alloys thereof.

4. The hydrogen peroxide sensitive metal nanoparticle of claim 1, wherein the metal nanoparticle has a diameter of 5-100 nm.

5. The hydrogen peroxide sensitive metal nanoparticle of claim 1, wherein the agglomerate has a size of 50 to 600 nm.

6. The hydrogen peroxide sensitive metal nanoparticle of claim 1, wherein the agglomerate has a light absorbance which is higher than a light absorbance of the hydrogen peroxide sensitive metal nanoparticle prior to the forming of the agglomerate in a visible light region of about 600 nm or more or in a near infrared region.

7. The hydrogen peroxide sensitive metal nanoparticle of claim 6, wherein the light absorbance of the agglomerate is higher by 50-100% than the light absorbance of the hydrogen peroxide sensitive metal nanoparticle prior to the forming of the agglomerate.

8. The hydrogen peroxide sensitive metal nanoparticle of claim 1, wherein the agglomerate generates heat when irradiated with light in a visible light region of 600 nm or more or in a near infrared region.

9. A hydrogen peroxide detecting system comprising:
    a medium containing the hydrogen peroxide sensitive metal nanoparticle of claim 1;
    a laser; and
    a temperature measuring device.

10. The detecting system of claim 9, wherein the laser generates a wavelength of 600 to 1100 nm.

11. A method of manufacturing a hydrogen peroxide sensitive metal nanoparticle, comprising:
    manufacturing a metal nanoparticle with a stabilizing ligand bonded to a surface thereof;
    replacing the stabilizing ligand with a hydrogen peroxide reactive ion that is capable of being oxidized by reacting with hydrogen peroxide;
    and producing the hydrogen peroxide sensitive metal nanoparticle of claim 1.

12. The method of claim 11, wherein the stabilizing ligand comprises a citrate ligand, an alkyl thiolate ligand, or an aryl thiolate ligand.

13. The method of claim 11, wherein the manufacturing of the metal nanoparticle comprises:
    dissolving a metal precursor in a solvent to form a metal precursor solution; and
    adding a reductant to the metal precursor solution thereby reducing the metal precursor.

14. The method of claim 13, wherein the metal precursor comprises a chloroauric acid, silver nitrate, Platinum (IV) chloride or titanium butoxide.

15. The method of claim 13, wherein the solvent comprises water or alcohol.

16. The method of claim 13, wherein the reductant comprises trisodium citrate, lithium aluminum hydride, nascent atomic hydrogen, sodium amalgam, sodium borohydride, tin (II) chloride, sodium sulfide, hydrazine, zinc-mercury amalgam, diisobutylaluminum hydride, Lindlar's catalyst, an oxalic acid, a formic acid or an ascorbic acid.

17. The method of claim 11, wherein the metal nanoparticle has a diameter of about 5 to about 100 nm.

18. The hydrogen peroxide sensitive metal nanoparticle of claim 1, wherein exposure to hydrogen peroxide causes the hydrogen peroxide reactive ion to lose an electrical charge.

19. The hydrogen peroxide sensitive metal nanoparticle of claim 1, wherein exposure to hydrogen peroxide causes the hydrogen peroxide reactive ion to disassociate from the metal nanoparticle.

20. An agglomerate of metal nanoparticles formed by exposing the hydrogen peroxide sensitive metal nanoparticle of claim 1 to hydrogen peroxide.

21. The agglomerate of metal nanoparticles of claim 20 having a light absorbance which is higher than a light absorbance of the hydrogen peroxide sensitive metal nanoparticles prior to the forming of the agglomerate in a visible light region of 600 nm or more or in a near infrared region.

22. The agglomerate of metal nanoparticles of claim 20, wherein the light absorbance of the agglomerate of metal nanoparticles is higher by 50-100% than the light absorbance of the hydrogen peroxide sensitive metal nanoparticle prior to the forming of the agglomerate.

23. A method of detecting hydrogen peroxide comprising the steps of:
    exposing the hydrogen peroxide sensitive metal nanoparticle of claim 1 to a sample; and
    measuring a light absorbance in a visible light region of about 600 nm or more or in a near infrared region,
    wherein a change in the light absorbance is an indication of an existence of hydrogen peroxide in the sample.

24. The method of detecting hydrogen peroxide of claim 23, further comprising the step of:
    exposing the hydrogen peroxide sensitive metal nanoparticle to light having a wavelength in a visible light region of about 600 nm or more or in a near infrared region.

* * * * *